US012672968B1

(12) United States Patent
Lenzi et al.

(10) Patent No.: US 12,672,968 B1
(45) **Date of Patent: *Jul. 7, 2026**

(54) POWERED EXOSKELETON WITH TORQUE-SENSITIVE ACTUATION

(71) Applicant: University of Utah Research Foundation, Salt Lake City, UT (US)

(72) Inventors: Tommaso Lenzi, Salt Lake City, UT (US); Lukas R. Gabert, Salt Lake City, UT (US); Brendon M. Ortolano, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/081,549

(22) Filed: Mar. 17, 2025

(51) Int. Cl.
A61H 3/00 (2006.01)
A61F 2/64 (2006.01)
(Continued)

(52) U.S. Cl.
CPC .................. *A61F 2/70* (2013.01); *A61F 2/64* (2013.01); *A61H 3/00* (2013.01); *B25J 9/0006* (2013.01);
(Continued)

(58) Field of Classification Search
CPC ... A61H 3/00; A61H 2205/102; B25J 9/0006; A61F 2002/5038; A61F 2/60; A61F 2/64; A61F 2/70
See application file for complete search history.

(56) References Cited

U.S. PATENT DOCUMENTS 5,020,790 A * 6/1991 Beard .................. A61F 5/0102
623/24
5,327,795 A * 7/1994 Katahira ................ B23Q 5/402
74/89.3
(Continued)

FOREIGN PATENT DOCUMENTS

CN        114191152        3/2022
EP          4454628        10/2024
(Continued)

OTHER PUBLICATIONS

Best et al., Data-Driven Variable Impedance Control of a Powered Knee-Ankle Prosthesis for Adaptive Speed and Incline Walking, IEEE Transactions on Robotics, 2022, 19 pages.
(Continued)

*Primary Examiner* — Timothy A Stanis
(74) *Attorney, Agent, or Firm* — Thorpe North & Western, LLP

(57) ABSTRACT
A powered exoskeleton device includes an external frame, operable to be secured to a limb of a user. An artificial joint body pivotal about a joint axis is connected to the external frame to transmit force through the external frame to the limb of the user. A transmission transfers force from an input motor to the artificial joint body. The transmission includes a crank, pivotally coupled to the artificial joint body about a crank axle rotatable about a crank axis. A primary compression spring is carried by the artificial joint body and is operably coupled to the crank. Movement of the input motor results in the crank transferring force to the artificial joint body about the crank axle and through the primary compression spring to cause the artificial joint body to pivot about the joint axis, thus aiding the user is moving the limb.

19 Claims, 9 Drawing Sheets

(51) Int. Cl.

| | | |
|---|---|---|
| *A61F 2/70* | (2006.01) | |
| *B25J 9/00* | (2006.01) | |
| *A61F 2/50* | (2006.01) | |
| *A61F 2/60* | (2006.01) | |

(52) U.S. Cl.

CPC ................. *A61F 2002/5038* (2013.01); *A61F 2002/5072* (2013.01); *A61F 2002/607* (2013.01); *A61F 2002/608* (2013.01)

(56) References Cited

U.S. PATENT DOCUMENTS

| | | | | |
|---|---|---|---|---|
| 11,035,743 | B2 * | 6/2021 | Paine | H02K 7/06 |
| 2016/0158029 | A1 * | 6/2016 | Kuiken | A61F 2/64 |
| | | | | 623/24 |
| 2018/0055712 | A1 * | 3/2018 | Gayral | A61H 1/0266 |
| 2018/0098864 | A1 * | 4/2018 | Auberger | A61F 2/64 |
| 2018/0116828 | A1 * | 5/2018 | Quinn | B25J 9/0006 |
| 2021/0053208 | A1 * | 2/2021 | Paine | B25J 9/0006 |
| 2021/0338458 | A1 | 11/2021 | Lenzi et al. | |
| 2022/0323240 | A1 | 10/2022 | Seifert et al. | |
| 2023/0050006 | A1 | 2/2023 | Pickerill et al. | |
| 2023/0092812 | A1 | 3/2023 | Goldfarb et al. | |
| 2023/0398003 | A1 | 12/2023 | Gregg et al. | |
| 2024/0026945 | A1 * | 1/2024 | Braun | A61F 5/01 |

FOREIGN PATENT DOCUMENTS

| | | |
|---|---|---|
| JP | 4744589 | 8/2011 |
| JP | 5095582 | 12/2012 |
| KR | 102265666 | 6/2021 |

OTHER PUBLICATIONS

Culver et al., A new approach to a powered knee prosthesis: Layering powered assistance onto strictly passive prosthesis behavior, Wearable Technologies, vol. 4, e21, 2023, 21 pages.

Elery et al., Design and Benchtop Validation of a Powered Knee-Ankle Prosthesis with High-Torque, Low-Impedance Actuators, ResearchGate Conference Paper, 2018, 9 pages, https://www.researchgate.net/publication/327805193.

Lee et al., The effects of swing assistance in a microprocessor-controlled transfemoral prosthesis on walking at varying speeds and grades, Wearable Technologies, vol. 4, e9, 2023, 13 pages.

Lenzie et al., Actively Variable Transmission for Robotic Knee Prostheses, ResearchGate Conference Paper, 2017, 8 pages, https://www.researchgate.net/publication/317585732.

Mooney, The Use of Series Compliance and Variable Transmission Elements in the Design of a Powered Knee Prosthesis, SB Mechanical Engineering, Massachusetts Institute of Technology, 2012, 73 pages.

Martinez-Villalpando et al., Agonist-antagonist active knee prosthesis: A preliminary study in level-ground walking, Journal of Rehabilitation Research & Development, vol. 46, No. 3, 2009, 13 pages.

Sanz-Morere et al., An active knee orthosis with a variable transmission ratio through a motorized dual clutch, Mechatronics 94, 103018, 2023, 13 pages, https://doi.org/10.1016/j.mechatronics.2023.103018.

Sun et al., Variable Transmission Series Elastic Actuator for Robotic Prosthesis, IEEE International Conference on Robotics and Automation (ICRA), 2018, 1 page, Abstract only.

Tessari et al., Knee prosthesis powered by a fully integrated and highly back-drivable electro-hydrostatic actuator, Mechatronics 91, 102972, 2023, 12 pages, https://doi.org/10.1016/j.mechatronics.2023.102972.

Zhu et al., Design and experiment of a variable stiffness prosthetic knee joint using parallel elastic actuation, Robotics and Autonomous Systems 171, 104566, 2024, 14 pages, https://doi.org/10.1016/j.robot.2023.104566.

Brackx et al.,Design of a Modular Add-on Compliant Actuator to Convert an Orthosis into an Assistive Exoskeleton, IEEE RAS & EMBS International Conference on Biomedical Robotics and Biomechatronics, 2014, 6 pages.

* cited by examiner

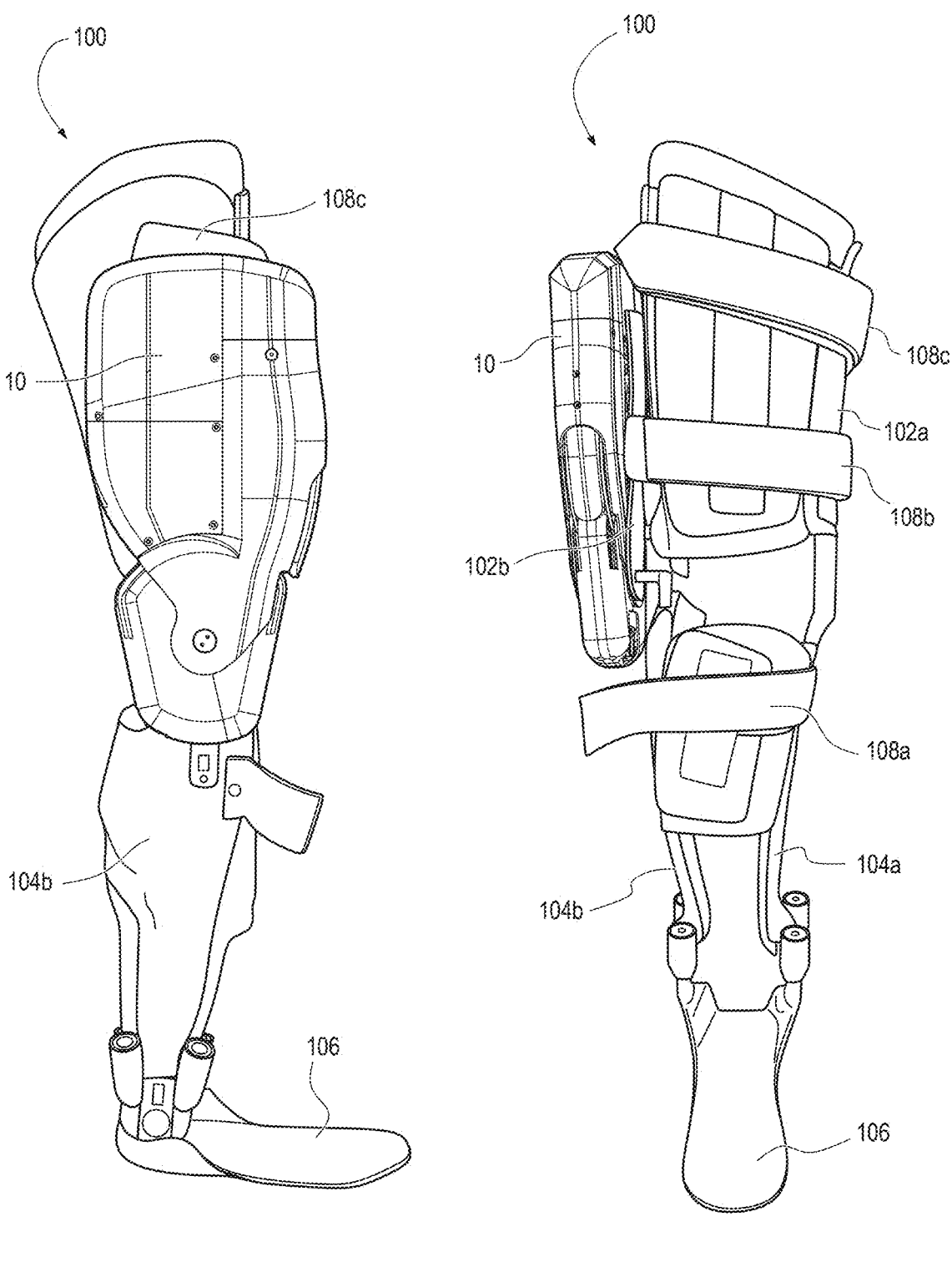
FIG. 1          FIG. 2

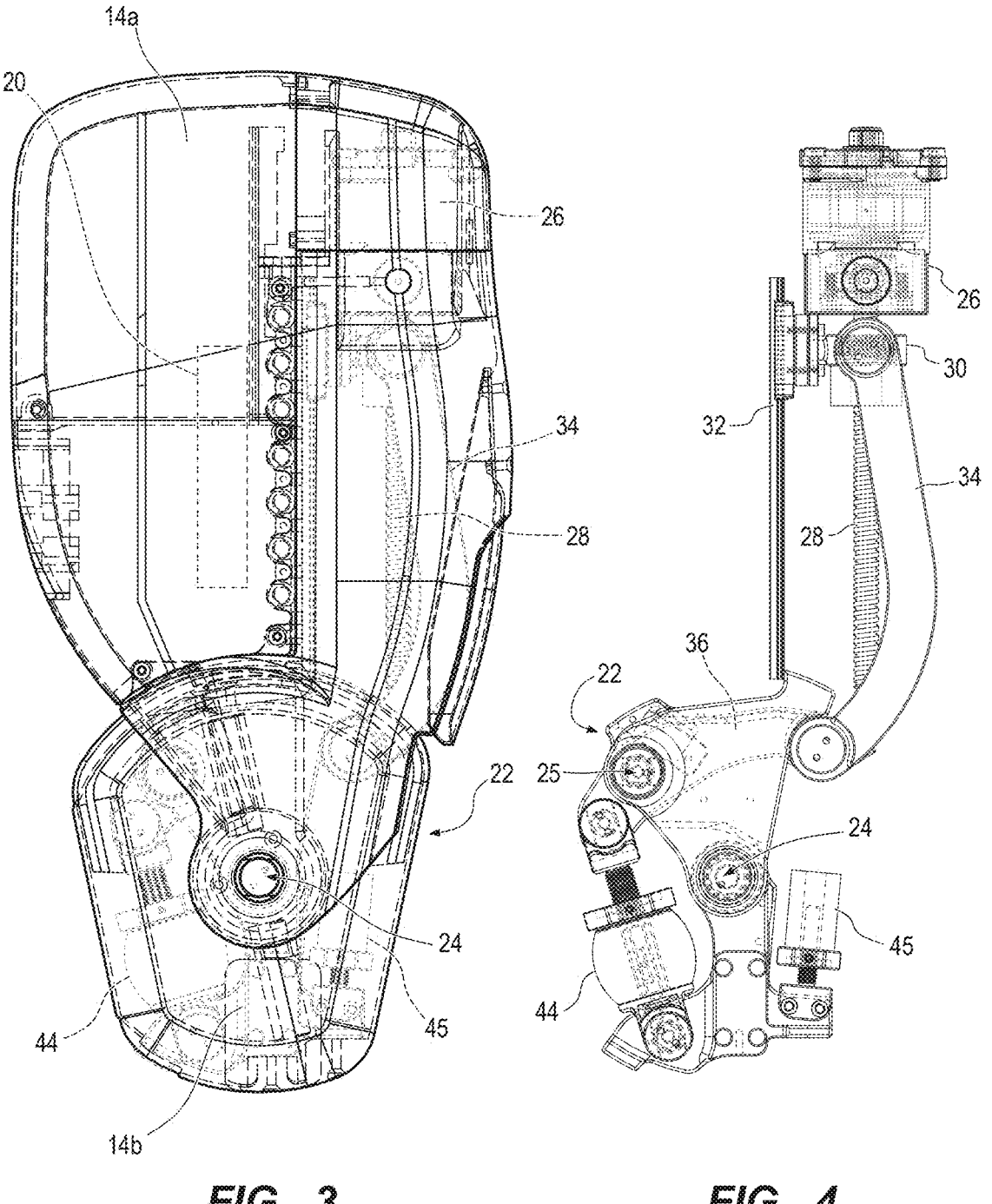
FIG. 3                              FIG. 4

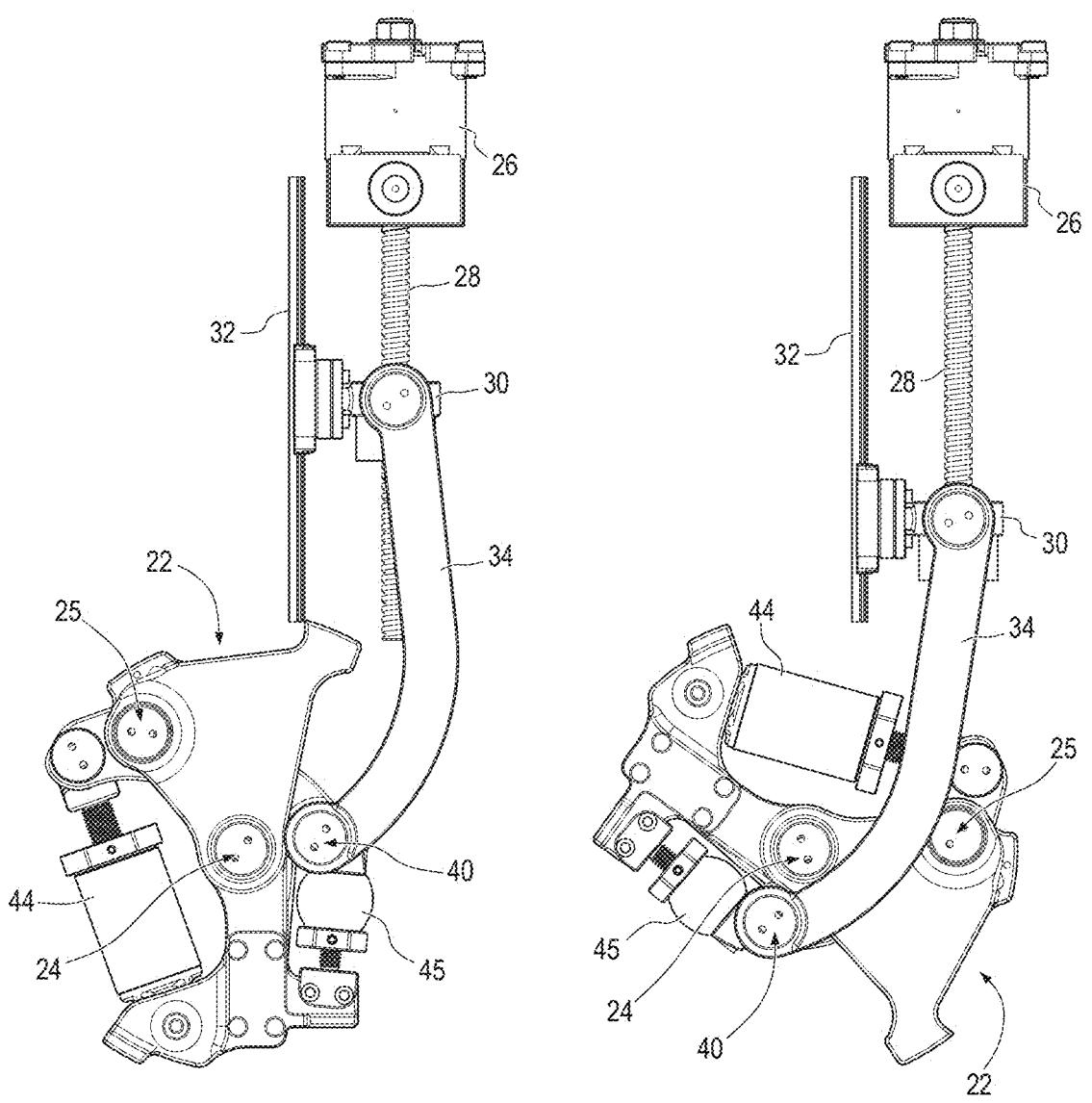
FIG. 5                    FIG. 6

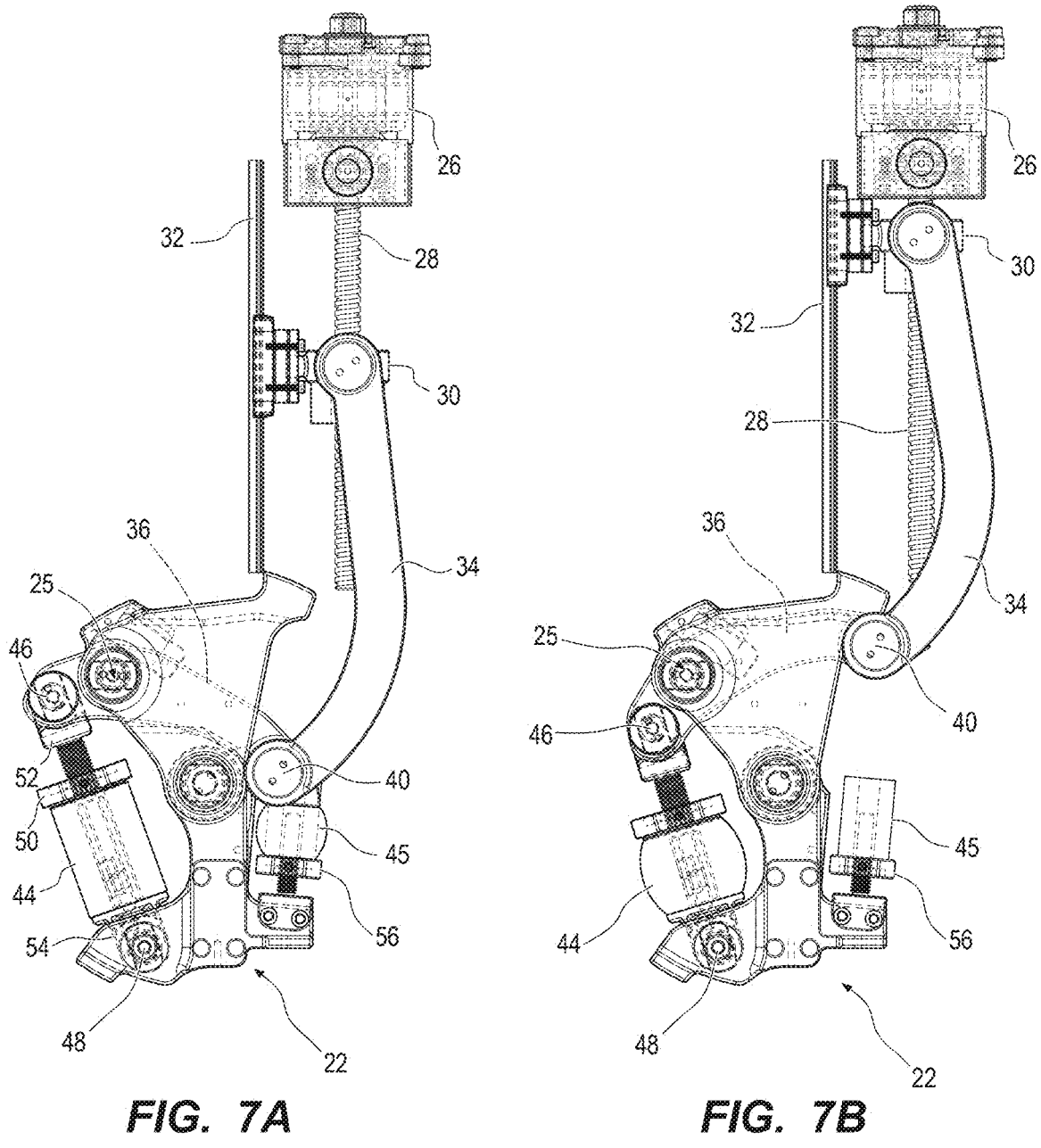
FIG. 7A　　　　　FIG. 7B

━━━━ Knee Torque        Time [s]
∙∙∙∙∙∙ Knee Angle

POWERED EXOSKELETON WITH TORQUE-SENSITIVE ACTUATION

STATEMENT REGARDING FEDERALLY SPONSORED RESEARCH OR DEVELOPMENT

This invention was made with government support under 2046287 awarded by the National Science Foundation. The government has certain rights in the invention.

CROSS REFERENCE TO RELATED APPLICATIONS

Not Applicable.

NAMES OF THE PARTIES TO A JOINT RESEARCH AGREEMENT

Not applicable.

INCORPORATION BY REFERENCE STATEMENT

Not applicable.

BACKGROUND

Powered exoskeletons offer a promising solution to restore ambulation ability to individuals with disabilities. Unfortunately, the clinical success of available exoskeletons is limited by their large weight. Wearing an exoskeleton adds mass and impedance to the user's legs, which has negative effects on gait efficiency and balance. Often, the negative effects of the added exoskeleton mass cancel out the positive effects of the exoskeleton assistance. Reducing the weight and impedance of powered exoskeletons without sacrificing assistive torque and power is an open challenge. As such, there remains a need for lightweight, low-impedance powered exoskeletons. To address this problem, researchers have proposed advanced actuation systems including series and parallel elastic actuators, clutchable actuators, quasi-direct drives and two-speed gearboxes. These advanced actuators allow for lighter exoskeletons compared to using conventional actuators based on highly geared electric motors. However, even with these advanced actuators, the weight of powered exoskeletons remains a problem.

SUMMARY

This invention relates to a powered exoskeleton that can include an external frame operable to be secured to a limb of a user. An artificial joint body can be connected to the external frame and can be operable to transmit force through the external frame to the limb of the user. The artificial joint body can be pivotal about a joint axis and can receive input from an input motor. A transmission can be operable to transfer force from the input motor to the artificial joint body. The transmission can include a crank, pivotally coupled to the artificial joint body about a crank axle rotatable about a crank axis. The input motor can be operably coupled to the crank such that rotation of the input motor causes the crank to pivot about the crank axis. A primary compression spring can be carried by the artificial joint body, the primary compression spring being operably coupled to the crank. Movement of the input motor can result in the crank transferring force to the artificial joint body about the crank axle and through the primary compression spring to cause the artificial joint body to pivot about the joint axis.

In accordance with another aspect of the technology, a powered exoskeleton device is provided, including an external frame, operable to be secured to a limb of a user and an artificial joint body, connected to the external frame and operable to transmit force through the external frame to the limb of the user. The artificial joint body can be pivotal about a joint axis and can receive input from an input motor. A transmission can be operable to transfer force from the input motor to the artificial joint body. The transmission can include a crank, pivotally coupled to the artificial joint body about a crank axle rotatable about a crank axis. The input motor can be rotatably coupled to the crank such that movement of the input motor causes the crank to pivot about the crank axis. The crank axis and the joint axis can be laterally displaced from one another. A primary compression spring can be rotatably coupled to the artificial joint body and can be rotatably coupled to the crank, the primary compression spring being continually compressed between the crank and the artificial joint body through a full range of motion of the artificial joint body. A secondary compression spring can be carried by the artificial joint body and can be separably contactable by the crank. A ball screw spindle can be rotatable by the input motor. A ball nut can be threadably engaged with the ball screw spindle such that rotation of the ball screw spindle results in translation of the ball nut. A connecting arm can extend between the ball nut and the crank to translate movement of the ball nut into movement of the crank. The input motor can include a rotor that can be fixed relative to the ball screw spindle such that movement of the rotor results directly in movement of the ball screw spindle. Movement of the ball screw spindle can result in the crank transferring force to the artificial joint body about the crank axle and through the primary compression spring to cause the artificial joint body to pivot about the joint axis. A primary pre-loader can be threadably engageable with the primary compression spring such that rotating the primary pre-loader results in pre-loading the primary compression spring by compressing the primary compression spring. A secondary pre-loader can be threadably engageable with the secondary compression spring such that rotating the secondary pre-loader results in pre-loading the secondary compression spring by compressing the secondary compression spring. A range of motion of the artificial joint body includes: i) a low transmission ratio configuration in which the crank engages both the primary and secondary compression springs; and ii) a high transmission ratio configuration in which the crank remains engaged with the primary compression spring and is separated from contact with the secondary compression spring.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

BRIEF DESCRIPTION OF THE DRAWINGS

FIG. 1 is a side view of an exoskeleton in accordance with the present technology.

FIG. 2 is a front view of the exoskeleton of FIG. 1.

FIG. 3 is a side view of a powered artificial joint body operably coupled to the exoskeleton of FIG. 1.

FIG. 4 is a side view of the joint body of FIG. 3, shown with various protective frames/covers removed.

FIG. 5 is a side view of the joint body of FIG. 4 in a fully extended configuration.

FIG. 6 is a side view of the joint body of FIG. 5 in a fully flexed configuration.

FIG. 7A is a side view of the joint body of FIG. 4 in a low-transmission ratio configuration.

FIG. 7B is a side view of the joint body of FIG. 4 in a high-transmission ratio configuration.

Figures 8A, 8B:
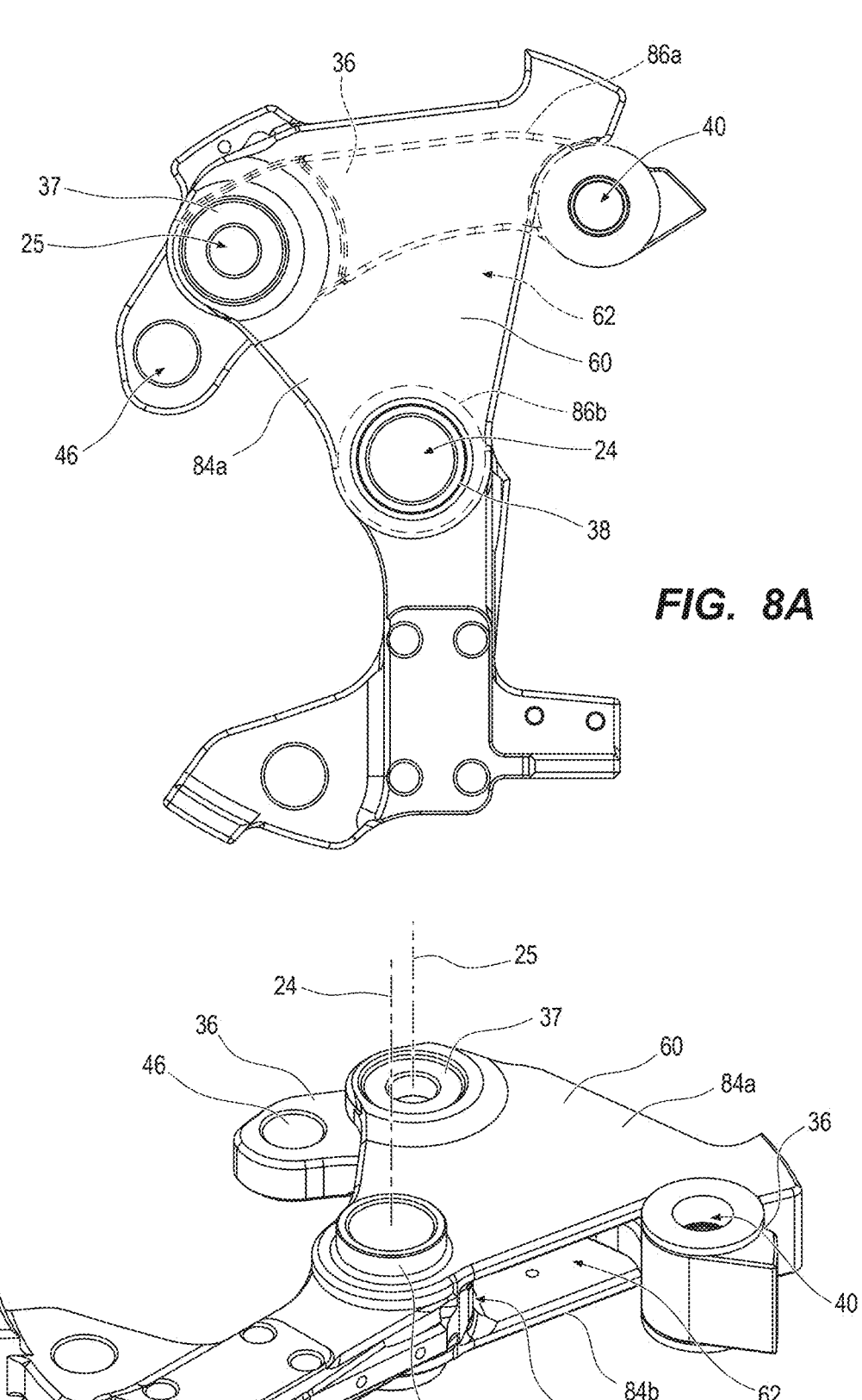
FIG. 8A is a side view of a main frame and a crank of the joint body of FIG. 4.
FIG. 8B is a perspective view of the main frame and the crank of FIG. 8A.

These drawings are provided to illustrate various aspects of the invention and are not intended to be limiting of the scope in terms of dimensions, materials, configurations, arrangements or proportions unless otherwise limited by the claims.

DETAILED DESCRIPTION

While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

Definitions

In describing and claiming the present invention, the following terminology will be used.

The singular forms "a," "an," and "the" include plural referents unless the context clearly dictates otherwise. Thus, for example, reference to "an axle" can include reference to one or more of such axles, if the context so dictates.

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context.

As used herein, the term "about" is used to provide flexibility and imprecision associated with a given term, metric or value. The degree of flexibility for a particular variable can be readily determined by one skilled in the art. However, unless otherwise enunciated, the term "about" generally connotes flexibility of less than 2%, and most often less than 1%, and in some cases less than 0.01%.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

As used herein, the term "at least one of" is intended to be synonymous with "one or more of." For example, "at least one of A, B and C" explicitly includes only A, only B, only C, or combinations of each.

Numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

EXAMPLE EMBODIMENTS

The present technology is directed to a powered knee exoskeleton with a torque-sensitive actuator module attached to carbon fiber interfaces, which transfer torque from the actuator to the user's limbs. This technology has potential applications in the medical field, such as assisting in ambulation for patients with paraplegia or hemiparesis, or increasing human performance of able-bodied individuals.

The present technology includes powered exoskeleton with torque sensitive actuation which is a novel actuation technology that combines the benefits of elastic actuators and variable transmission systems. One exemplary powered exoskeleton device 100 is shown in FIGS. 1 and 2. The device can include an external frame that can be secured to or about a limb of a user (not shown). The external frame can include, for example, first and second upper frame sections 102a, 102b that can be cinched about the user's upper leg (e.g., thigh) via straps 108b, 108c. The straps can be secured using known fasteners, such as hook-and-loop fasteners, buckles, snaps, etc. First and second lower frame sections 104a, 104b can be cinched about the user's lower leg (e.g., calf) via strap 108a. The user's foot can rest upon platform 106. An artificial joint body 10 can be connected to the external frame and can be operable to transmit force through the external frame to the limb of the user, thereby assisting the user in ambulation. As shown in FIG. 3, the artificial joint body can include outer cover or frame members 14a, 14b, etc. The artificial joint body can be connected to the external frame via the outer cover or frame members such that they can transfer force to the external frame of the exoskeleton, or various structure can extend from the artificial joint body, through the outer cover or frame members, to connect with the external frame.

Various electronic components are shown schematically at 20 in FIG. 3. These can include power sources, control boards, encoders, communication modules, etc., that can be carried within the device to provide functionality to the motors, feedback mechanisms, controllers, etc., as will be readily appreciated by one of ordinary skill in the art having possession of this disclosure. Note that neither the position nor the size of these components is precisely represented in the schematic representation of FIG. 3.

Select internal components of the device are shown in FIGS. 3 and 4, including an artificial joint body 22 that can be pivotal about a joint axis 24. An input motor 26 can, in one aspect, provide rotational output to a ball screw spindle 28. As the motor actuates, the ball screw spindle is rotated, which in turn rotates ball nut 30, which is threadably engaged with the ball screw spindle. Ball nut 30 can be restrained by linear guide 32. As such, rotation of the ball screw spindle results in translation of the ball nut along the linear guide. One or more connecting arms 34 can extend between the ball nut and a crank 36 (discussed in more detail below) to translate movement of the ball nut into movement of the crank. This, in turn, results in movement, e.g., rotation, of the artificial joint body 22 about the joint axis 24 and, accordingly, rotation of the exoskeleton's lower, e.g., calf, portion relative to its upper, e.g., thigh, portion.

FIGS. 5 and 6 collectively illustrate the range of motion through which the artificial joint body 22 is capable of traveling. FIG. 5 represents the fully extended position, e.g., the position of the joint body when the user is standing, while FIG. 6 illustrates the fully flexed position, e.g., the position of the joint body when the exoskeleton is replicating a fully bent knee. The crank 36 is rotatable about a crank axis 25. In the embodiments shown, the joint axis 24 and the crank axis 25 are laterally displaced from one another. This allows the crank to rotate at a differing speed or angle than does the joint body as a whole. The location of pin 25 can define the trajectory of point 40 as a response to changes in output torque. The trajectory of point 40 can also define the transmission ratio (along with other parameters). In other words, the location of pin 25 has huge effects on the surface shown in FIG. 11A).

FIGS. 7A and 7B illustrate the artificial joint body 22 in the fully extended position, with FIG. 7A representing a low transmission ratio configuration, and FIG. 7B representing a high transmission ratio configuration. The prosthesis can include a torque-sensitive transmission comprised of a variety of components that continuously and passively vary the transmission ratio of the prosthesis. Because some energy is stored in compression springs (as discussed in more detail below), there is no unified transmission ratio; in other words, velocity ratio and torque ratio are different quantities. Accordingly, as used herein, the term "transmission ratio" refers to torque ratio.

The transmission is operable to transfer force from the input motor 26 to the artificial joint body 22 while varying the torque ratio. In one example, the transmission can include, without limitation, the crank 36, and one or more compression springs 44, 45, each of which is discussed in further detail below. The crank 36 can be coupled to a crank axle 37 (see FIGS. 8A and 8B) rotatable about the crank axis 25. The input motor 26 can be operably coupled to the crank such that movement of the input motor causes the crank to pivot about the crank axis. In the example shown, the input motor is operably connected to connecting arm 34, which is rotatably coupled to the crank at 40. A primary compression spring 44 can be carried by the artificial joint body and can be operably coupled to the crank.

In use, actuation of input motor 26 results in rotation of the ball screw spindle 28, which results in ball nut 30 translating up or down relative to the spindle, which in turn results in connecting arm 34 applying force to the crank 36. As the crank moves, it transfers force to the artificial joint body 22 about the crank axle 37 (FIGS. 8A and 8B) and through the primary compression spring 44 to cause the artificial joint body to pivot about the joint axis 24.

The primary compression spring 44 can be coupled on one end to the crank 36 and on an opposing end to a portion of the artificial joint body (e.g., one or more of the frames or covers 14a, 14b rigidly fixed relative to the joint body or to the main frame 60 in FIGS. 8A and 8B). In one embodiment (FIG. 7A), the primary compression spring is rotatably coupled to the crank at 46 and rotatably coupled to the portion of the artificial joint body at 48. These rotatable/pivotal connections prevent the primary compression spring from buckling during movement of the joint. The primary compression spring can be continually compressed between the crank and the artificial joint body through a full range of motion of the artificial joint body. A primary pre-loader 50 can be threadably engageable with the primary compression spring 44. Rotation of the primary pre-loader results in pre-loading the primary compression spring by compressing the primary compression spring. The primary pre-loader can be threaded into a base 52 (FIG. 7A) that can be rotatably attached to the crank 36 at 46. An opposing cap 54 can threadably engage the pre-loader and can be rotatably attached to the artificial joint body at 46.

The transmission can also include a secondary compression spring 45, carried by the artificial joint body 22 and contactable by the crank 36. A secondary pre-loader 56 can be threadably engageable with the secondary compression spring. Adjusting the secondary pre-loader, when the device is in the position shown in FIGS. 5 and 7A, results in applying, or lessening, a pre-load experienced by the secondary compression spring as it is compressed between the crank and the artificial joint body.

Generally, the crank 36 is in separable contact with the secondary compression spring 45. In other words, one end of the secondary compression spring is uncoupled relative to the crank. A range of motion of the artificial joint body 22 can include: i) a low transmission ratio configuration in which the crank 36 engages both the primary 44 and secondary 45 compression springs (see FIGS. 5 and 7A, for example); and ii) a high transmission ratio configuration in which the crank remains engaged with the primary compression spring and is separated from contact with the secondary compression spring (see FIGS. 4 and 7B, for example). The system is continuously variable through the range of motion, e.g., between and including these high and low configurations. In one aspect of the technology, a torque produced by the pre-load force of the secondary compression spring by the secondary pre-loader about the crank axis is substantially equal to the torque required to be produced by the motor about the crank axis to rotate the crank to a position that is equal to the preloaded position when the secondary spring is absent. In another aspect of the technology, a pre-load force applied to the secondary compression spring by the secondary pre-loader is substantially equal to a force required to rotate the artificial joint body to a position in which the crank no longer contacts the secondary compression spring.

The current system is thus a revolute torque-sensitive joint including a crank 36 loaded by two compression springs (44, 45). FIGS. 8A and 8B show the crank 36 in greater detail, along with main frame 60. The main frame can be coupled to or carried by the joint body 22 in a number of suitable manners. The crank can be rotatably coupled to the main frame via crank axle 37, such that the two rotate relative to one another about axis 25. The main frame can include a crank slot 62 defined at least partially by two opposing side walls 84a, 84b, such that the crank is restrained within the crank slot by the two sidewalls. The crank slot can be further defined by an upper 86a and lower 86b abutment (see FIG. 8A), which serve to restrain rotatable motion of the crank therebetween. Thus, the crank is restrained within the crank slot by the two side walls and the upper and lower abutment.

First and second ends of the crank 36 can extend from opposing sides of the crank slot 62. The primary compression spring (not shown in these figures) can be rotatably coupled to the first end of the crank outside the crank slot at 46 and a connecting arm can be rotatably connected to the second end of the crank outside the crank slot at 40. This arrangement allows the crank to be compactly installed within the main frame so that an overall thickness of the artificial joint body can be minimized, thus reducing an overall weight of the exoskeleton.

Figure 9:
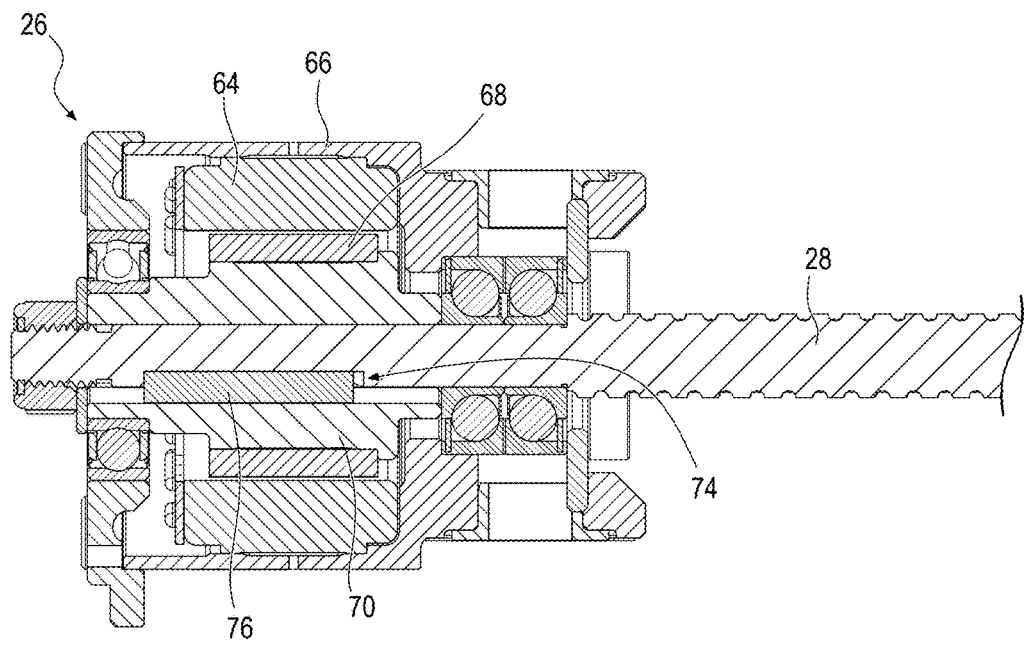
FIG. 9 is a side, partially sectioned view of an input motor in accordance with an aspect of the technology.

FIG. 9 illustrates further details of one example of motor 26. The motor can include a stator 64 within a stator housing 66. The stator housing can be coupled directly to the artificial joint body 22 (not shown in this figure) and bonded or fixed to the stator. A rotor 68 can rotate within the stator, and can have a rotor adaptor 70 fixed or bonded thereto. The rotor adaptor can include a key 76 fixed therein. The spindle 28 can include a spindle key slot 74 formed therein, with the key 76 positioned in the spindle key slot to thereby fixedly attach the rotor adaptor to the spindle.

Thus, the rotor 68 of the input motor 26 is fixed relative to the ball screw spindle 28, without the presence of any transmission components, such as gears or couplers, such that movement of the rotor of the input motor results directly in movement of the ball screw spindle. The lack of gears, couplers, and the related additional bearings results in a device with reduced complexity and reduced acoustic noise levels. Notably, although an electric motor is exemplified above, and in the figures, other input motors can be used. Non-limiting examples of suitable input motors can include pneumatic actuators, hydraulic actuators, and the like as long as the chosen input motor can produce force for transfer by the transmission as described herein.

Figure 10A:
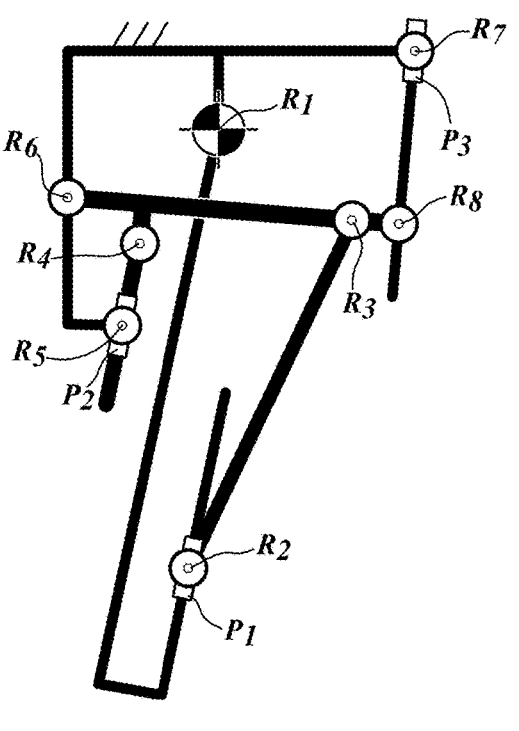
FIG. 10A is a kinematic diagram of the torque-sensitive actuator of the present technology, in the low-transmission ratio of FIG. 7A.
Figure 10B:
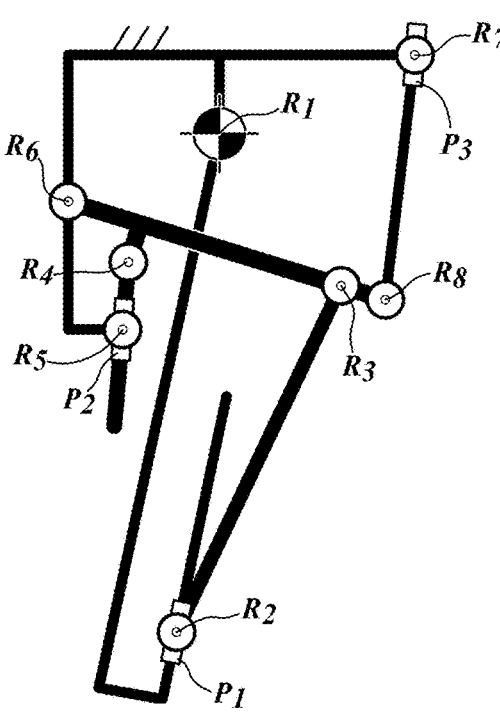
FIG. 10B is a kinematic diagram of the torque-sensitive actuator of the present technology, in the high-transmission ratio of FIG. 7B.

FIGS. 10A and 10B are kinematic diagrams of the torque-sensitive behavior of the present technology. FIG. 10A illustrates the low-transmission ratio configuration, corresponding to the physical configuration shown in FIG. 7A. FIG. 10B illustrates the high-transmission ratio configuration, corresponding to the physical configuration of FIG. 7B. The current torque-sensitive actuator is based on a five-bar linkage with two degrees of freedom. The first degree of freedom is the angle of the knee joint. The other is the angle of the crank. Intuitively, the mechanism acts like a four-bar linkage with variable geometry. The ball screw ($P_1$) (28 in FIG. 7A) drives the connecting bars ($\overline{R_2R_3}$) (34 in FIG. 7A), which push and pull on the crank ($\overrightarrow{R_6R_3}$) (36 in FIG. 7A). The crank ($\overline{R_6R_3}$), the primary spring ($\overline{R_5P_2R_4}$), and the secondary spring ($\overline{R_7P_3R_8}$) constitute the torque-sensitive mechanism, which is fully contained within the thigh portion of the device (e.g., the artificial joint body 22). To generate extension torque, the motor pulls on the connecting bars and crank, inducing a moment about the crank axis ($R_6$) (25 in FIG. 7A). As a result, the primary spring ($P_3$) (44 in FIG. 7A) compresses and the secondary spring ($P_2$) (45 in FIG. 7A) extends, shifting the location of the output crank axis ($R_3$) (40 in FIG. 7A) downward and away from the joint center ($R_1$) (24 in FIG. 7A), thus increasing the moment arm and transmission ratio. Therefore, the transmission ratio is proportional to the output extension torque.

In one embodiment, the secondary spring is only active during the initial range of motion of the torque-sensitive mechanism and serves two different purposes. The first function is shock absorption. The secondary spring provides a soft end-stop, reducing shock loads and acoustic noise when the crank returns to the low-transmission ratio position during the unloading phases. The second function is stiffness modulation. Combined, the primary spring (44) and secondary springs (45) act as a dual-rate degressive spring system. At low knee extension torques (one such configuration shown in FIG. 7A), both the primary and secondary springs are in contact with the crank. In this case, the two springs act in parallel, resulting in high equivalent torsional stiffness about the crank axis ($R_6$) (25 in FIG. 7A). Above a certain knee extension torque, the secondary spring is no longer in contact with the crank (FIG. 7B), and only the primary spring provides reaction force. In this case, the equivalent torsional stiffness about the crank axis ($R_6$) (25 in FIG. 7A) is lower. Due to this softening stiffness behavior (i.e., degressive spring), the torque-sensitive actuator is less sensitive at lower torques than at higher torques. This variable sensitivity allows for full modulation of the transmission ratio during ambulation while ensuring a high dynamic response to changes in torque.

In one example the primary (44) and secondary (45) springs can be formed as polyurethane cylinders. Eladur springs manufactured by Veith are used in some embodiments and have shown to produce longer life, high energy density, and low-noise operation than conventional systems. The springs, however, can be formed from a variety of materials and in a variety of configurations, including coil springs, leaf springs, metallic springs, and the like.

There is synergy between the actuator's low transmission ratio and the actuator's torque sensitivity. When abruptly applying a torque, the torque-sensitive linkage will move. This means that some portion of the power from the motor is going into internal dynamic terms such as moving the motor and linkages, rather than to the user's limbs. By minimizing the reflected inertia of the motor, the dynamic terms are also minimized, e.g. smaller forces are used to achieve the same acceleration. Therefore, the torque-sensitive linkage deflects much quicker and the user feels the torque from the motor sooner. This allows the system to reduce the reflected inertia of the motor, which in turn allows the present system to be even more aggressive (e.g., higher range of motion, higher change in transmission ratio), which allows the use of an even smaller motor with even less inertia. Thus, the two systems synergize.

Figure 11A:
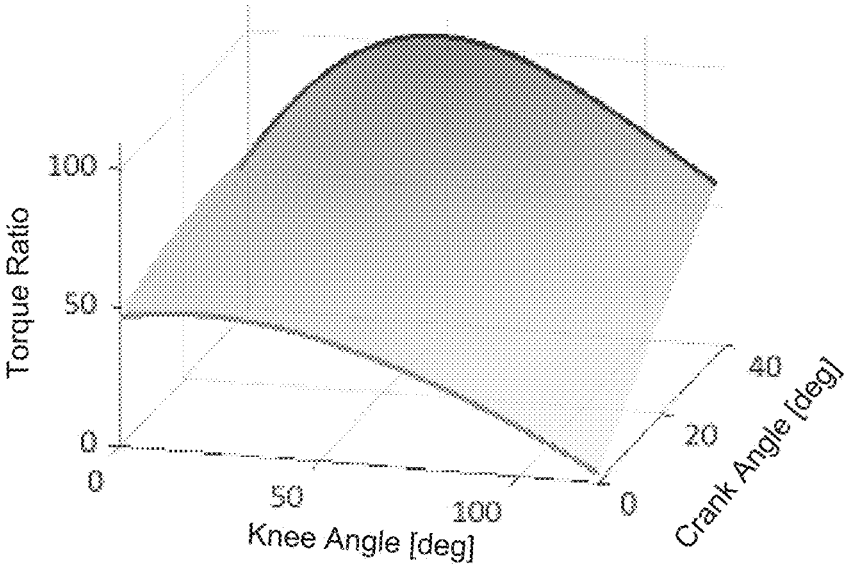
FIG. 11A is a data chart illustrating transmission ratio as a function of knee joint angle and crank angle in accordance with one aspect of the technology.
Figure 11B:
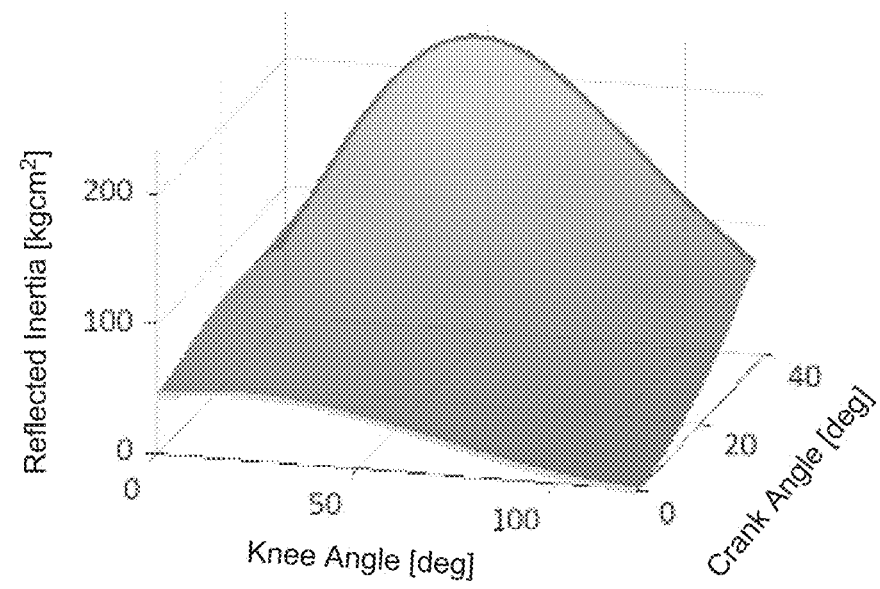
FIG. 11B is a data chart illustrating reflected inertia as a function of knee joint angle and crank angle in accordance with one aspect of the technology.
Figure 11C:
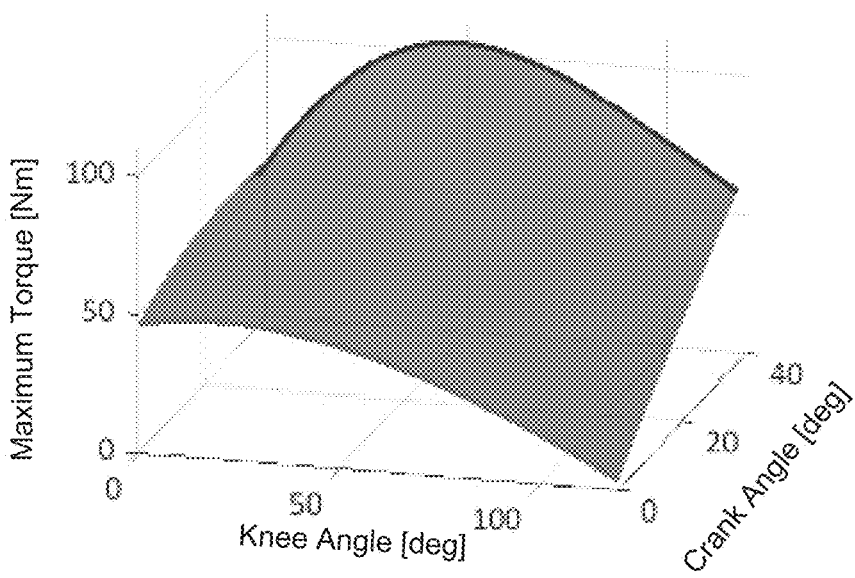
FIG. 11C is a data chart illustrating maximum torque as a function of knee joint angle and crank angle in accordance with one aspect of the technology.
Figure 12A:
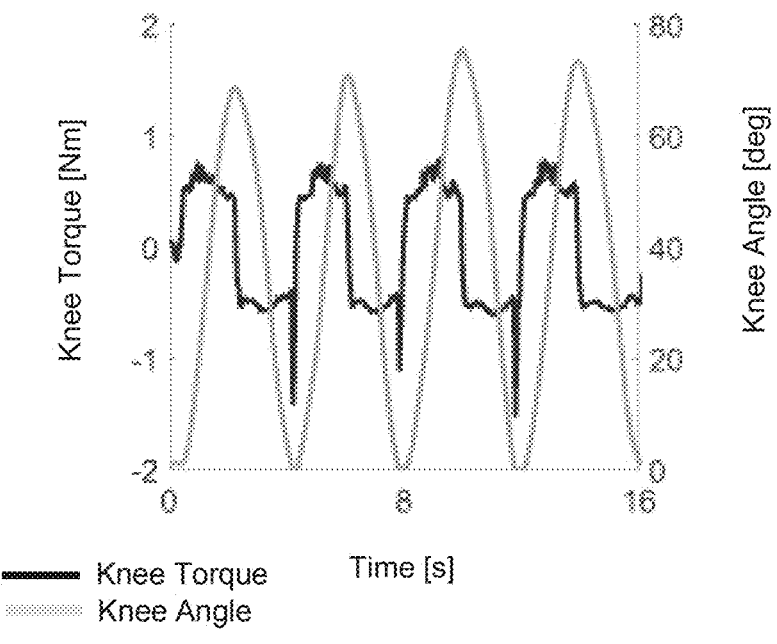
FIG. 12A is a data chart illustrating knee torque and knee angle vs. time in accordance with one benchtop experiment.
Figure 12B:
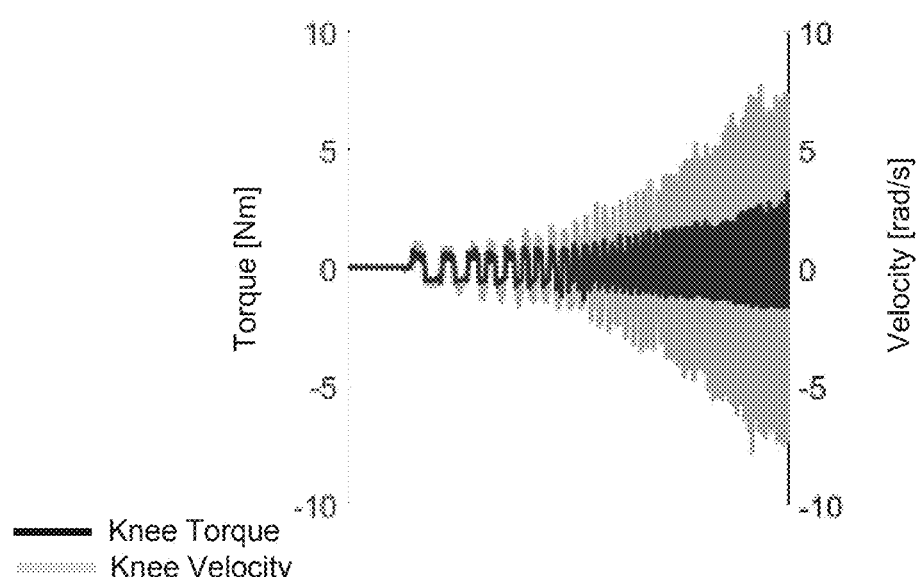
FIG. 12B is a data chart illustrating knee torque vs. velocity associated with the benchtop experiment data of FIG. 12A.
Figure 12C:
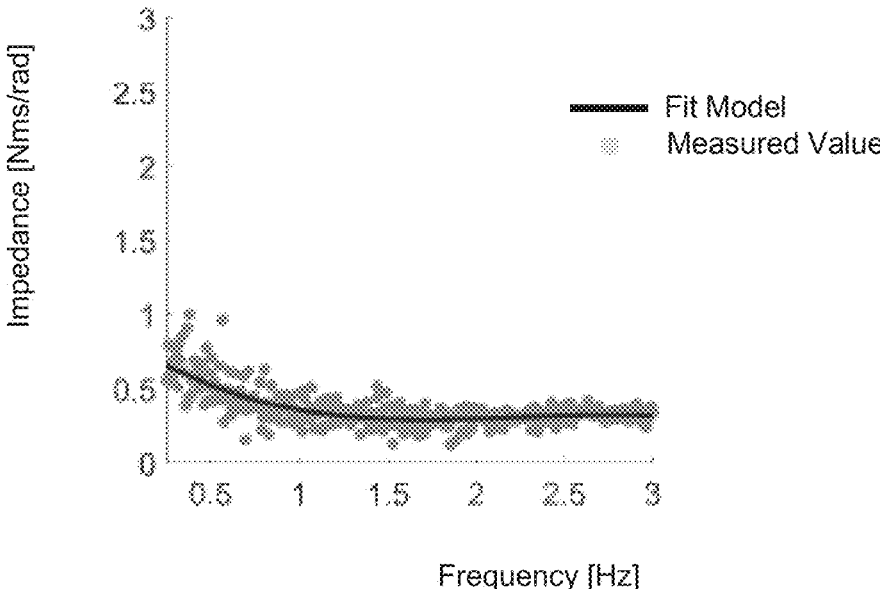
FIG. 12C is a data chart illustrating impedance vs. frequency associated with the benchtop experiment data of FIG. 12A.

FIGS. 11A-11C illustrate torque ratio, reflected inertia and maximum torque, respectively, vs. knee angle and crank angle from one exemplary arrangement of the exoskeleton device. While the embodiments above are discussed in association with a knee prosthesis, the present technology can be incorporated into prostheses for a variety of joints. Generally, the location of the crank axis 25 defines the trajectory of point 40 as a response to changes in output torque. The trajectory of point 40 defines the transmission ratio (along with some other parameters). In other words, the location of joint axis 25 effects the surface shown in FIGS. 11A-11C. The size and placement of crank 36 determine the device's range of motion and the device's minimum and maximum torque ratio (FIG. 11A). Different biological joints have different ranges of motion and will likely have a desirable peak torque ratio at a different joint angle. For example, an elbow/forearm exoskeleton will likely require a similar range of motion as a knee prosthesis, but the peak torque ratio may be at a more flexed angle if predominantly elbow extension torques are applied. As a result, the location of kinematic point 40 may move slightly. The kinematics of the system would likely not change for application to a different joint, but the angles/lengths of the realized implementation may differ.

While motor 26 is shown and described herein as an electrical motor providing rotational output, it is understood that a variety of motor types can be utilized to provide movement to the crank 36, including hydraulic motors, pneumatic motors, etc.

Reference was made to the examples illustrated in the drawings and specific language was used herein to describe the same. It will nevertheless be understood that no limitation of the scope of the technology is thereby intended. Alterations and further modifications of the features illustrated herein and additional applications of the examples as illustrated herein are to be considered within the scope of the description.

Furthermore, the described features, structures, or characteristics may be combined in any suitable manner in one or more examples. In the preceding description, numerous specific details were provided, such as examples of various configurations to provide a thorough understanding of examples of the described technology. It will be recognized, however, that the technology may be practiced without one or more of the specific details, or with other methods, components, devices, etc. In other instances, well-known structures or operations are not shown or described in detail to avoid obscuring aspects of the technology.

Although the subject matter has been described in language specific to structural features and/or operations, it is to be understood that the subject matter defined in the appended claims is not necessarily limited to the specific features and operations described above. Rather, the specific features and acts described above are disclosed as example forms of implementing the claims. Numerous modifications and alternative arrangements may be devised without departing from the spirit and scope of the described technology.

What is claimed is:

1. A powered exoskeleton device, comprising:
   an external frame, operable to be secured to a limb of a user;
   an artificial joint body, connected to the external frame and operable to transmit force through the external frame to the limb of the user, the artificial joint body being pivotal about a joint axis;
   an input motor;
   a transmission, operable to transfer force from the input motor to the artificial joint body, the transmission including:
      a crank, pivotally coupled to the artificial joint body about a crank axle rotatable about a crank axis, the input motor being operably coupled to the crank with a series of linkages such that rotation of the input motor causes the crank to pivot about the crank axis; and
      a primary compression spring, carried by the artificial joint body, the primary compression spring being operably coupled to the crank; and
   a secondary compression spring, carried by the artificial joint body and contactable by the crank
   wherein movement of the input motor results in the crank transferring force to the artificial joint body about the crank axle and through the primary compression spring to cause the artificial joint body to pivot about the joint axis.

2. The device of claim 1, wherein the primary compression spring is coupled on one end to the crank and on an opposing end to a portion of the artificial joint body.

3. The device of claim 2, wherein the primary compression spring is rotatably coupled to the crank and to the portion of the artificial joint body.

4. The device of claim 2, further comprising a primary pre-loader threadably engageable with the primary compression spring, wherein rotating the primary pre-loader results in pre-loading the primary compression spring by compressing the primary compression spring.

5. The device of claim 1, wherein the primary compression spring is continually compressed between an output side of the crank and the artificial joint body through a full range of motion of the artificial joint body.

6. The device of claim 1, further comprising a secondary pre-loader threadably engageable with the secondary compression spring, wherein rotating the secondary pre-loader results in pre-loading the secondary compression spring by compressing the secondary compression spring when in contact with the crank.

7. The device of claim 6, wherein the crank is in separable contact with the secondary compression spring.

8. The device of claim 7, wherein a range of motion of the artificial joint body includes: i) a low transmission ratio configuration in which the crank engages both the primary and secondary compression springs; and ii) a high transmission ratio configuration in which the crank remains engaged with the primary compression spring and is separated from contact with the secondary compression spring.

9. The device of claim 1, wherein the joint axis and the crank axis are laterally displaced from one another.

10. The device of claim 1, further comprising:

a ball screw spindle, rotatable by the input motor;

a ball nut, threadably engaged by the ball screw spindle, wherein rotation of the ball screw spindle results in translation of the ball nut; and a connecting arm, extending between the ball nut and the crank to translate movement of the ball nut into movement of the crank, wherein the input motor includes a rotor, the rotor being fixed relative to the ball screw spindle such that movement of the rotor of the input motor results directly in movement of the ball screw spindle.

11. The device of claim 10, further comprising a rotor adaptor fixedly bonded to the rotor and having an adaptor key slot formed therein, and wherein the ball screw spindle includes a spindle key slot formed therein, and further comprising a key positioned in each of the adaptor key slot and the spindle key slot to fixedly attach them one to another.

12. The device of claim 1, wherein the artificial joint body includes a main frame, the crank being rotatably coupled to the main frame about the crank axis, the main frame including a crank slot defined at least partially by two opposing sidewalls, the crank restrained within the crank slot by the two sidewalls.

13. The device of claim 12, wherein the crank slot is further defined by an upper and lower abutment, and wherein rotatable motion of the crank is restrained by the upper and lower abutment.

14. The device of claim 12, wherein a first and second end of the crank extend from opposing sides of the crank slot, and wherein the primary compression spring is rotatably coupled to the first end of the crank outside the crank slot and a connecting arm is rotatably connected to the second end of the crank outside the crank slot.

15. A powered exoskeleton device, comprising:

an external frame, operable to be secured to a limb of a user;

an artificial joint body, connected to the external frame and operable to transmit force through the external frame to the limb of the user, the artificial joint body being pivotal about a joint axis;

an input motor; and a transmission, operable to transfer force from the input motor to the artificial joint body, the transmission including:

a crank, pivotally coupled to the artificial joint body about a crank axle rotatable about a crank axis, the input motor being rotatably coupled to the crank such that movement of the input motor causes the crank to pivot about the crank axis, the crank axis and the joint axis being laterally displaced from one another; and a primary compression spring, rotatably coupled to the artificial joint body and rotatably coupled to the crank, the primary compression spring being continually compressed between the crank and the artificial joint body through a full range of motion of the artificial joint body;

a secondary compression spring, carried by the artificial joint body and separably contactable by the crank;

a ball screw spindle, rotatable by the input motor;

a ball nut, threadably engaged with the ball screw spindle such that rotation of the ball screw spindle results in translation of the ball nut; and a connecting arm, extending between the ball nut and the crank to translate movement of the ball nut into movement of the crank;

the input motor including a rotor, the rotor being fixed relative to the ball screw spindle such that movement of the rotor results directly in movement of the ball screw spindle;

wherein movement of the ball screw spindle results in the crank transferring force to the artificial joint body about the crank axle and through the primary compression spring to cause the artificial joint body to pivot about the joint axis;

a primary pre-loader threadably engageable with the primary compression spring, wherein rotating the primary pre-loader results in pre-loading the primary compression spring by compressing the primary compression spring; and a secondary pre-loader threadably engageable with the secondary compression spring, wherein rotating the secondary pre-loader results in pre-loading the secondary compression spring by compressing the secondary compression spring;

wherein a range of motion of the artificial joint body includes: i) a low transmission ratio configuration in which the crank engages both the primary and secondary compression springs; and ii) a high transmission ratio configuration in which the crank remains engaged with the primary compression spring and is separated from contact with the secondary compression spring.

16. The device of claim 15, further comprising a rotor adaptor fixedly bonded to the rotor and having an adaptor key slot formed therein, and wherein the ball screw spindle includes a spindle key slot formed therein, and further comprising a key positioned in each of the adaptor key slot and the spindle key slot to fixedly attach them one to another.

17. The device of claim 15, wherein the artificial joint body includes a main frame, the crank being rotatably coupled to the main frame about the crank axis, the main frame including a crank slot defined at least partially by two opposing sidewalls, the crank restrained within the crank slot by the two sidewalls.

18. The device of claim 17, wherein the crank slot is further defined by an upper and lower abutment, and wherein rotatable motion of the crank is restrained by the upper and lower abutment.

19. A powered exoskeleton device, comprising:

an external frame, operable to be secured to a limb of a user;

an artificial joint body, connected to the external frame and operable to transmit force through the external frame to the limb of the user, the artificial joint body being pivotal about a joint axis;

an input motor; and a transmission, operable to transfer force from the input motor to the artificial joint body, the transmission including:

a crank, pivotally coupled to the artificial joint body about a crank axle rotatable about a crank axis, the input motor being operably coupled to the crank with a series of linkages such that rotation of the input motor causes the crank to pivot about the crank axis;

a primary compression spring, carried by the artificial joint body, the primary compression spring being operably coupled to the crank;

a ball screw spindle, rotatable by the input motor;

a ball nut, threadably engaged by the ball screw spindle, wherein rotation of the ball screw spindle results in translation of the ball nut;

a connecting arm, extending between the ball nut and the crank to translate movement of the ball nut into movement of the crank, and a rotor adaptor fixedly bonded to the rotor and having an adaptor key slot formed therein, and wherein the ball screw spindle includes a spindle key slot formed therein, and further comprising a key positioned in each of the adaptor key slot and the spindle key slot to fixedly attach them one to another, wherein the input motor includes a rotor, the rotor being fixed relative to the ball screw spindle such that movement of the rotor of the input motor results directly in movement of the ball screw spindle, wherein movement of the input motor results in the crank transferring force to the artificial joint body about the crank axle and through the primary compression spring to cause the artificial joint body to pivot about the joint axis.

\* \* \* \* \*